(12) United States Patent
Sutton, II et al.

(10) Patent No.: US 7,546,457 B2
(45) Date of Patent: Jun. 9, 2009

(54) SYSTEM AND METHOD FOR EXECUTION OF A SECURED ENVIRONMENT INITIALIZATION INSTRUCTION

(75) Inventors: James A. Sutton, II, Portland, OR (US); David W. Grawrock, Aloha, OR (US)

(73) Assignee: Intel Corporation, Santa Clara, CA (US)

( * ) Notice: Subject to any disclaimer, the term of this patent is extended or adjusted under 35 U.S.C. 154(b) by 156 days.

(21) Appl. No.: 11/096,618

(22) Filed: Mar. 31, 2005

(65) Prior Publication Data

US 2005/0182940 A1 Aug. 18, 2005

Related U.S. Application Data

(63) Continuation of application No. 10/112,169, filed on Mar. 29, 2002, now Pat. No. 7,069,442.

(51) Int. Cl.
*H04L 29/00* (2006.01)
*G06F 21/00* (2006.01)

(52) U.S. Cl. ........................ 713/164; 713/190
(58) Field of Classification Search .................. 713/190
See application file for complete search history.

(56) References Cited

U.S. PATENT DOCUMENTS

| | | | |
|---|---|---|---|
| 3,699,532 A | 10/1972 | Schaffer et al. | |
| 3,996,449 A | 12/1976 | Attanasio et al. | |
| 4,037,214 A | 7/1977 | Birney et al. | |
| 4,162,536 A | 7/1979 | Morley | |
| 4,207,609 A | 6/1980 | Luiz et al. | |
| 4,247,905 A | 1/1981 | Yoshida et al. | |
| 4,276,594 A | 6/1981 | Morley | |
| 4,278,837 A | 7/1981 | Best | |
| 4,307,447 A | 12/1981 | Provanzano et al. | |
| 4,319,323 A | 3/1982 | Ermolovich et al. | |
| 4,347,565 A | 8/1982 | Kaneda et al. | |
| 4,366,537 A | 12/1982 | Heller et al. | |
| 4,403,283 A | 9/1983 | Myntti et al. | |
| 4,419,724 A | 12/1983 | Branigin et al. | |
| 4,430,709 A | 2/1984 | Schleupen et al. | |
| 4,521,852 A | 6/1985 | Guttag | |

(Continued)

FOREIGN PATENT DOCUMENTS

DE 4217444 12/1992

(Continued)

OTHER PUBLICATIONS

Berg, Cliff, "How Do I Create a Signed Applet?", Dr. Dobb's Journal, (Aug. 1997), pp. 1-9.

(Continued)

*Primary Examiner*—Matthew B Smithers
(74) *Attorney, Agent, or Firm*—Thomas R. Lane

(57) ABSTRACT

A method and apparatus for initiating secure operations in a microprocessor system is described. In one embodiment, one initiating logical processor initiates the process by halting the execution of the other logical processors, and then loading initialization and secure virtual machine monitor software into memory. The initiating processor then loads the initialization software into secure memory for authentication and execution. The initialization software then authenticates and registers the secure virtual machine monitor software prior to secure system operations.

19 Claims, 8 Drawing Sheets

U.S. PATENT DOCUMENTS

| | | | |
|---|---|---|---|
| 4,571,672 A | 2/1986 | Hatada et al. | |
| 4,759,064 A | 7/1988 | Chaum | |
| 4,795,893 A | 1/1989 | Ugon | |
| 4,802,084 A | 1/1989 | Ikegaya et al. | |
| 4,825,052 A | 4/1989 | Chemin et al. | |
| 4,907,270 A | 3/1990 | Hazard | |
| 4,907,272 A | 3/1990 | Hazard | |
| 4,910,774 A | 3/1990 | Barakat | |
| 4,975,836 A | 12/1990 | Hirosawa et al. | |
| 5,007,082 A | 4/1991 | Cummins | |
| 5,022,077 A | 6/1991 | Bealkowski et al. | |
| 5,075,842 A | 12/1991 | Lai | |
| 5,079,737 A | 1/1992 | Hackbarth | |
| 5,187,802 A | 2/1993 | Inoue et al. | |
| 5,230,069 A | 7/1993 | Brelsford et al. | |
| 5,237,616 A | 8/1993 | Abraham et al. | |
| 5,255,379 A | 10/1993 | Melo | |
| 5,287,363 A | 2/1994 | Wolf et al. | |
| 5,293,424 A | 3/1994 | Holtey et al. | |
| 5,295,251 A | 3/1994 | Wakui et al. | |
| 5,317,705 A | 5/1994 | Gannon et al. | |
| 5,319,760 A | 6/1994 | Mason et al. | |
| 5,361,375 A | 11/1994 | Ogi | |
| 5,386,552 A | 1/1995 | Garney | |
| 5,421,006 A | 5/1995 | Jablon et al. | |
| 5,434,999 A | 7/1995 | Goire et al. | |
| 5,437,033 A | 7/1995 | Inoue et al. | |
| 5,442,645 A | 8/1995 | Ugon et al. | |
| 5,455,909 A | 10/1995 | Blomgren et al. | |
| 5,459,867 A | 10/1995 | Adams et al. | |
| 5,459,869 A | 10/1995 | Spilo | |
| 5,469,557 A | 11/1995 | Salt et al. | |
| 5,473,692 A | 12/1995 | Davis | |
| 5,479,509 A | 12/1995 | Ugon | |
| 5,504,922 A | 4/1996 | Seki et al. | |
| 5,506,975 A | 4/1996 | Onodera | |
| 5,511,217 A | 4/1996 | Nakajima et al. | |
| 5,522,075 A | 5/1996 | Robinson et al. | |
| 5,528,231 A | 6/1996 | Patarin | |
| 5,533,126 A | 7/1996 | Hazard et al. | |
| 5,555,385 A | 9/1996 | Osisek | |
| 5,555,414 A | 9/1996 | Hough et al. | |
| 5,560,013 A | 9/1996 | Scalzi et al. | |
| 5,564,040 A | 10/1996 | Kubala | |
| 5,566,323 A | 10/1996 | Ugon | |
| 5,568,552 A | 10/1996 | Davis | |
| 5,574,936 A | 11/1996 | Ryba et al. | |
| 5,582,717 A | 12/1996 | Di Santo | |
| 5,604,805 A | 2/1997 | Brands | |
| 5,606,617 A | 2/1997 | Brands | |
| 5,615,263 A | 3/1997 | Takahashi | |
| 5,628,022 A | 5/1997 | Ueno et al. | |
| 5,628,023 A | 5/1997 | Bryant et al. | |
| 5,633,929 A | 5/1997 | Kaliski, Jr. | |
| 5,657,445 A | 8/1997 | Pearce | |
| 5,668,971 A | 9/1997 | Neufeld | |
| 5,684,948 A | 11/1997 | Johnson et al. | |
| 5,706,469 A | 1/1998 | Kobayashi | |
| 5,717,903 A | 2/1998 | Bonola | |
| 5,720,609 A | 2/1998 | Pfefferle | |
| 5,721,222 A | 2/1998 | Bernstein et al. | |
| 5,729,760 A | 3/1998 | Poisner | |
| 5,737,604 A | 4/1998 | Miller et al. | |
| 5,737,760 A | 4/1998 | Grimmer, Jr. et al. | |
| 5,740,178 A | 4/1998 | Jacks et al. | |
| 5,752,046 A | 5/1998 | Oprescu et al. | |
| 5,757,919 A | 5/1998 | Herbert et al. | |
| 5,764,889 A | 6/1998 | Ault et al. | |
| 5,764,969 A | 6/1998 | Kahle et al. | |
| 5,796,835 A | 8/1998 | Saada | |
| 5,796,845 A | 8/1998 | Serikawa et al. | |
| 5,805,712 A | 9/1998 | Davis | |
| 5,809,546 A | 9/1998 | Greenstein et al. | |
| 5,825,875 A | 10/1998 | Ugon | |
| 5,825,880 A | 10/1998 | Sudia et al. | |
| 5,835,594 A | 11/1998 | Albrecht et al. | |
| 5,844,986 A | 12/1998 | Davis | |
| 5,852,717 A | 12/1998 | Bhide et al. | |
| 5,854,913 A | 12/1998 | Goetz et al. | |
| 5,867,577 A | 2/1999 | Patarin | |
| 5,872,994 A | 2/1999 | Akiyama et al. | |
| 5,890,189 A | 3/1999 | Nozue et al. | |
| 5,900,606 A | 5/1999 | Rigal | |
| 5,901,225 A | 5/1999 | Ireton et al. | |
| 5,903,752 A | 5/1999 | Dingwall et al. | |
| 5,919,257 A | 7/1999 | Trostle | |
| 5,935,242 A | 8/1999 | Madany et al. | |
| 5,935,247 A | 8/1999 | Pai et al. | |
| 5,935,249 A | 8/1999 | Stern et al. | |
| 5,937,063 A | 8/1999 | Davis | |
| 5,953,502 A | 9/1999 | Helbig, Sr. | |
| 5,956,408 A | 9/1999 | Arnold | |
| 5,970,147 A | 10/1999 | Davis et al. | |
| 5,978,475 A | 11/1999 | Schneier et al. | |
| 5,978,481 A | 11/1999 | Ganesan et al. | |
| 5,987,557 A | 11/1999 | Ebrahim | |
| 5,987,604 A | 11/1999 | Edrich | |
| 6,014,745 A | 1/2000 | Ashe | |
| 6,035,374 A | 3/2000 | Panwar et al. | |
| 6,044,478 A | 3/2000 | Green | |
| 6,055,637 A | 4/2000 | Hudson et al. | |
| 6,058,478 A | 5/2000 | Davis | |
| 6,061,794 A | 5/2000 | Angelo | |
| 6,075,938 A | 6/2000 | Bugnion et al. | |
| 6,085,296 A | 7/2000 | Karkhanis et al. | |
| 6,088,262 A | 7/2000 | Nasu | |
| 6,092,095 A | 7/2000 | Maytal | |
| 6,093,213 A | 7/2000 | Favor et al. | |
| 6,101,584 A | 8/2000 | Satou et al. | |
| 6,108,644 A | 8/2000 | Goldschlag et al. | |
| 6,115,816 A | 9/2000 | Davis | |
| 6,125,430 A | 9/2000 | Noel et al. | |
| 6,131,166 A | 10/2000 | Wong-Isley | |
| 6,148,379 A | 11/2000 | Schimmel | |
| 6,158,546 A | 12/2000 | Hanson et al. | |
| 6,173,417 B1 | 1/2001 | Merrill | |
| 6,175,924 B1 | 1/2001 | Arnold | |
| 6,175,925 B1 | 1/2001 | Nardone et al. | |
| 6,178,509 B1 | 1/2001 | Nardone | |
| 6,182,089 B1 | 1/2001 | Ganapathy et al. | |
| 6,188,257 B1 | 2/2001 | Buer | |
| 6,192,455 B1 | 2/2001 | Bogin et al. | |
| 6,199,152 B1 | 3/2001 | Kelly et al. | |
| 6,205,550 B1 | 3/2001 | Nardone et al. | |
| 6,212,635 B1 | 4/2001 | Reardon | |
| 6,222,923 B1 | 4/2001 | Schwenk | |
| 6,249,872 B1 | 6/2001 | Wildgrube et al. | |
| 6,252,650 B1 | 6/2001 | Nakamura | |
| 6,269,392 B1 | 7/2001 | Cotichini et al. | |
| 6,272,533 B1 | 8/2001 | Browne et al. | |
| 6,272,637 B1 | 8/2001 | Little et al. | |
| 6,275,933 B1 | 8/2001 | Fine et al. | |
| 6,282,650 B1 | 8/2001 | Davis | |
| 6,282,651 B1 | 8/2001 | Ashe | |
| 6,282,657 B1 | 8/2001 | Kaplan et al. | |
| 6,292,874 B1 | 9/2001 | Barnett | |
| 6,301,646 B1 | 10/2001 | Hostetter | |
| 6,308,270 B1 | 10/2001 | Guthery et al. | |
| 6,314,409 B2 | 11/2001 | Schneck et al. | |
| 6,321,314 B1 | 11/2001 | Van Dyke | |
| 6,327,652 B1 | 12/2001 | England et al. | |
| 6,330,670 B1 | 12/2001 | England et al. | |
| 6,339,815 B1 | 1/2002 | Feng et al. | |
| 6,339,816 B1 | 1/2002 | Bausch | |

| | | | |
|---|---|---|---|
| 6,357,004 B1 | 3/2002 | Davis | |
| 6,363,485 B1 | 3/2002 | Adams | |
| 6,374,286 B1 | 4/2002 | Gee et al. | |
| 6,374,317 B1 | 4/2002 | Ajanovic et al. | |
| 6,378,068 B1 | 4/2002 | Foster | |
| 6,378,072 B1 | 4/2002 | Collins et al. | |
| 6,389,537 B1 | 5/2002 | Davis et al. | |
| 6,397,242 B1 | 5/2002 | Devine et al. | |
| 6,397,379 B1 | 5/2002 | Yates, Jr. et al. | |
| 6,412,035 B1 | 6/2002 | Webber | |
| 6,421,702 B1 | 7/2002 | Gulick | |
| 6,435,416 B1 | 8/2002 | Slassi | |
| 6,445,797 B1 | 9/2002 | McGough et al. | |
| 6,463,535 B1 | 10/2002 | Drews et al. | |
| 6,463,537 B1 | 10/2002 | Tello | |
| 6,499,123 B1 | 12/2002 | McFarland et al. | |
| 6,505,279 B1 | 1/2003 | Phillips et al. | |
| 6,507,904 B1 | 1/2003 | Ellison et al. | |
| 6,529,909 B1 | 3/2003 | Bowman-Amuah | |
| 6,535,988 B1 | 3/2003 | Poisner | |
| 6,557,104 B2 | 4/2003 | Vu et al. | |
| 6,560,627 B1 | 5/2003 | McDonald et al. | |
| 6,609,199 B1 | 8/2003 | DeTreville | |
| 6,615,278 B1 | 9/2003 | Curtis | |
| 6,633,963 B1 | 10/2003 | Ellison et al. | |
| 6,633,981 B1 | 10/2003 | Davis | |
| 6,651,171 B1 | 11/2003 | England et al. | |
| 6,678,825 B1 | 1/2004 | Ellison et al. | |
| 6,684,326 B1 | 1/2004 | Cromer et al. | |
| 6,754,815 B1 | 6/2004 | Ellison et al. | |
| 6,760,441 B1 | 7/2004 | Ellison et al. | |
| 6,769,058 B1 | 7/2004 | Ellison et al. | |
| 6,795,905 B1 | 9/2004 | Ellison et al. | |
| 6,986,052 B1 * | 1/2006 | Mittal | 713/190 |
| 2001/0021969 A1 | 9/2001 | Burger et al. | |
| 2001/0027511 A1 | 10/2001 | Wakabayashi et al. | |
| 2001/0027527 A1 | 10/2001 | Khidekel et al. | |
| 2001/0037450 A1 | 11/2001 | Metlitski et al. | |
| 2002/0007456 A1 | 1/2002 | Peinado et al. | |
| 2002/0023032 A1 | 2/2002 | Pearson et al. | |
| 2002/0147916 A1 | 10/2002 | Strongin et al. | |
| 2002/0166061 A1 | 11/2002 | Falik et al. | |
| 2002/0169717 A1 | 11/2002 | Challener | |
| 2002/0184520 A1 | 12/2002 | Bush et al. | |
| 2003/0018892 A1 | 1/2003 | Tello | |
| 2003/0074648 A1 | 4/2003 | Cromer et al. | |
| 2003/0115453 A1 | 6/2003 | Grawrock | |
| 2003/0126442 A1 | 7/2003 | Glew et al. | |
| 2003/0126453 A1 | 7/2003 | Glew et al. | |
| 2003/0140238 A1 * | 7/2003 | Turkboylari | 713/193 |
| 2003/0159056 A1 | 8/2003 | Cromer et al. | |
| 2003/0188179 A1 | 10/2003 | Challener et al. | |
| 2003/0196085 A1 | 10/2003 | Lampson et al. | |
| 2004/0117539 A1 | 6/2004 | Bennett et al. | |

FOREIGN PATENT DOCUMENTS

| | | |
|---|---|---|
| EP | 0 473 913 A2 | 3/1992 |
| EP | 0 600 112 A1 | 6/1994 |
| EP | 0 892 521 A2 | 1/1999 |
| EP | 0 930 567 A3 | 7/1999 |
| EP | 0 961 193 A2 | 12/1999 |
| EP | 0 965 902 A2 | 12/1999 |
| EP | 1 030 237 A1 | 8/2000 |
| EP | 1 055 989 A1 | 11/2000 |
| EP | 1 056 014 A1 | 11/2000 |
| EP | 1 085 396 A1 | 3/2001 |
| EP | 1 146 715 A1 | 10/2001 |
| EP | 1 271 277 A2 | 1/2003 |
| JP | 2000076139 | 3/2000 |
| WO | WO 95/24696 A2 | 9/1995 |
| WO | WO 97/29567 A1 | 8/1997 |
| WO | WO 98/12620 A1 | 3/1998 |
| WO | WO 98/34365 A1 | 8/1998 |
| WO | WO 98/44402 A1 | 10/1998 |
| WO | WO 99/05600 A2 | 2/1999 |
| WO | WO 99/09482 A1 | 2/1999 |
| WO | WO 99/18511 A1 | 4/1999 |
| WO | WO 99/57863 A1 | 11/1999 |
| WO | WO 99/65579 A1 | 12/1999 |
| WO | WO 02/17555 A2 | 2/2000 |
| WO | WO 00/21238 A1 | 4/2000 |
| WO | WO 00/62232 A1 | 10/2000 |
| WO | WO 01/16772 A1 | 3/2001 |
| WO | WO 01/27723 A1 | 4/2001 |
| WO | WO 01/27821 A2 | 4/2001 |
| WO | WO 01/63994 A2 | 8/2001 |
| WO | WO 01/75564 A2 | 10/2001 |
| WO | WO 01/75565 A2 | 10/2001 |
| WO | WO 01/75595 A2 | 10/2001 |
| WO | WO 02/01794 A2 | 1/2002 |
| WO | WO 02/060121 A1 | 8/2002 |
| WO | WO 02/086684 A2 | 10/2002 |
| WO | WO 03/058412 A2 | 7/2003 |

OTHER PUBLICATIONS

Brands, Stefan, "Restrictive Blinding of Secret-Key Certificates", Springer-Verlag XP002201306, (1995),Chapter 3.

Chien, Andrew A., et al., "Safe and Protected Execution for the Morph/AMRM Reconfigurable Processor", 7th Annual IEEE Symposium, FCCM '99 Proceedings, XP010359180, ISBN 0-7695-0375-6, Los Alamitos, CA, (Apr. 21, 1999), pp. 209-221.

Compaq Computer Corporation, et al., "Trusted Computing Platform Alliance (TCPA) Main Specification Version 1.1a", (Dec. 2001), pp. 1-321.

Coulouris, G. et al., "Distributed Systems: Concepts and Design", 2nd Edition, Addison-Wesley Publishers Ltd., Essex, England, pp. 422-424 (1994).

Crawford, J., "Architecture of the Intel 80386", Proceedings of the IEEE International Conference on Computer Design: VLSI in Computers (ICCD '86), ISBN 0-8186-0735-1, pp. 155-160 (Oct. 6-9, 1986).

Davida, George I., et al., "Defending Systems Against Viruses through Cryptographic Authentication", Proceedings of the Symposium on Security and Privacy, IEEE Comp. Soc. Press, ISBN 0-8186-1939-2, (May 1989).

Fabry, R.S., "Capability-Based Addressing", Communications of the ACM, vol. 17, No. 7, pp. 403-412 (Jul. 1974).

Frieder, G., "The Architecture and Operational Characteristics of the VMX Host Machine", IEEE Proceedings of the 15th Annual Workshop on Microprogramming, pp. 9-16, (Oct. 5, 1982).

Goldberg, Robert P., "Survey of Virtual Machine Research", Computer Magazine, (Jun. 1974), pp. 34-35.

Gum, P. H., "System/370 Extended Architecture: Facilities for Virtual Machines", IBM J. Research Development, vol. 27, No. 6, (Nov. 1983), pp. 530-544.

Heinrich, Joe, "MIPS R4000 Microprocessor User's Manual, Second Edition", Chapter 4 "Memory Management", (Jun. 11, 1993), pp. 61-97.

Hewlett Packard Company, "Mobile Security Overview", pp. 1-9, (Sep. 2002).

IBM, "Information Display Technique for a Terminate Stay Resident Program IBM Technical Disclosure Bulletin", TDB-ACC-No. NA9112156, vol. 34, Issue 7A, (Dec. 1, 1991), pp. 156-158.

IBM Corporation, "IBM ThinkPad T30 Notebooks", IBM Product Specification, located at www-1.ibm.com/services/files/cisco_t30_spec_sheet_070202.pdf, pp. 1-6 (Jul. 2, 2002).

Intel Corporation, "Intel 82802AB/82802AC Firmware Hub (FWH)", Intel Product Datasheet, Document No. 290658-004, pp. 1-6, 17-28 (Nov. 2000).

Intel Corporation, "IA-64 System Abstraction Layer Specification", Intel Product Specification, Order No. 245359-001, 112 pages, Jan. 2000.

Intel Corporation, "Intel IA-64 Architecture Software Developer's Manual—vol. 2: IA-64 System Architecture", Intel Product Manual, Order No. 245318-001, pp. i, ii, 5.1-5.3, 11.1-11.8, 11.2-11.26, Jan. 2000.

Intel Corporation, "IA-32 Intel Architecture Software Developer's Manual—vol. 3: System Programming Guide", (2003) pp. 13-1 to 13-24.

Intel Corporation, "Intel386 DX Microprocessor 32-Bit CHMOS Microprocessor With Integrated Memory Management", (1995), pp. 5-56.

Karger, Paul A., et al., "A VMM Security Kernal for the VAX Architecture", Proceedings of the Symposium on Research in Security and Privacy, XP010020182, ISBN 0-8186-2060-9, Boxborough, MA, (May 7, 1990), pp. 2-19.

Kashiwagi, Kazuhiko, et al., "Design and Implementation of Dynamically Reconstructing System Software", Software Engineering Conference, Proceedings 1996 Asia-Pacific Seoul, South Korea Dec. 4-7, 1996, Los Alamitos, CA USA, IEEE Comput. Soc, US, ISBN 0-8186-7638-8, (1996).

Lawton, Kevin, et al., "Running Multiple Operating Systems Concurrently on an IA32 PC Using Virtualization Techniques", http://www.plex86.org/research/paper.txt, (Nov. 29, 1999), pp. 1-31.

Luke, Jahn, et al., "Replacement Strategy for Aging Avionics Computers", IEEE AES Systems Magazine, XP002190614, (Mar. 1999).

Menezes, Alfred J., et al., "Handbook of Applied Cryptography", CRC Press Series on Discrete Mathematics and its Applications, Boca Raton, FL, ISBN 0849385237, pp. 403-405, 475, 506-515, 570 (Oct. 1996).

Motorola, "M68040 User's Manual", (1993), pp. 1-1 to 8-32.

Nanba, S. et al., "VM/4: ACOS-4 Virtual Machine Architecture", IEEE Proceedings of the 12$^{th}$ Annual Symposium on Computer Architecture, pp. 171-178 (Jun. 1985).

Richt, Stefan, et al., "In-Circuit-Emulator Wird Echtzeittauglich", Elektronic, Franzis Verlag GMBH, Munchen, DE, vol. 40, No. 16, XP000259620, (Aug. 6, 1991), pp. 100-103.

Robin, John S., et al., "Analysis of the Pentium's Ability to Support a Secure Virtual Machine Monitor", Proceedings of the 9th USENIX Security Symposium, XP002247347, Denver, Colorado, (Aug. 14, 2000), pp. 1-17.

Rosenblum, M., "Virtual Platform: A Virtual Machine Monitor for Commodity PC", Proceedings of the 11th Hotchips Conference, (Aug. 17, 1999), pp. 185-196.

RSA Security Inc., "Hardware Authenticators", located at www.rsasecurity.com/node.asp?id=1158, pp. 1-2 (2004).

RSA Security Inc., "Software Authenticators", located at www.rsasecurity.com/node.asp?id=1313, pp. 1-2 (2004).

RSA Security Inc., "RSA SecurID Authenticators", located at www.rsasecurity.com/products/securid/datasheets/SID_DS_0103.pdf, pp. 1-2 (2003).

Saez, Sergio, et al., "A Hardware Scheduler for Complex Real-Time Systems", Proceedings of the IEEE International Symposium on Industrial Electronics, XP002190615,(Jul. 1999), pp. 43-48.

Schneier, B., "Applied Cryptography: Protocols, Algorithm, and Source Code in C", 2$^{nd}$ Edition, Wiley, John & Sons, Inc., ISBN 0471117099 (hardcover printing), pp. 47-52, 56-65, 169-187 (Oct. 1995).

Schneier, B., "Applied Cryptography: Protocols, Algorithm, and Source Code in C", 2$^{nd}$ Edition, Wiley, John & Sons, Inc., ISBN 0471128457 (softcover printing), pp. 28-33, 176-177, 216-217, 461-473, 518-522 (Nov. 1995).

Sherwood, Timothy, et al., "Patchable Instruction ROM Architecture", Department of Computer Science and Engineering, University of California, San Diego, La Jolla, CA, (Nov. 2001).

IPEA/US, International Preliminary Examination Report for International Application No. PCT/US03/08762, 4 pages, Jan. 19, 2005.

* cited by examiner

200 # SYSTEM AND METHOD FOR EXECUTION OF A SECURED ENVIRONMENT INITIALIZATION INSTRUCTION

RELATED APPLICATIONS

This application is a continuation of, and claims the priority of, application Ser. No. 10/112,169, filed on 29 Mar. 2002, entitled "SYSTEM AND METHOD FOR EXECUTION OF A SECURED ENVIRONMENT INITIALIZATION INSTRUCTION, which issued on Jun. 27, 2006 as U.S. Pat. No. 7,069,442.

FIELD

The present invention relates generally to microprocessor systems, and more specifically to microprocessor systems that may operate in a trusted or secured environment.

BACKGROUND

The increasing number of financial and personal transactions being performed on local or remote microcomputers has given impetus for the establishment of "trusted" or "secured" microprocessor environments. The problem these environments try to solve is that of loss of privacy, or data being corrupted or abused. Users do not want their private data made public. They also do not want their data altered or used in inappropriate transactions. Examples of these include unintentional release of medical records or electronic theft of funds from an on-line bank or other depository. Similarly, content providers seek to protect digital content (for example, music, other audio, video, or other types of data in general) from being copied without authorization.

Existing trusted systems may utilize a complete closed set of trusted software. This method is relatively simple to implement, but has the disadvantage of not allowing the simultaneous use of common, commercially available operating system and application software. This disadvantage limits the acceptance of such a trusted system.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

The following description describes techniques for initiating a trusted or secured environment in a microprocessor system. In the following description, numerous specific details such as logic implementations, software module allocation, encryption techniques, bus signaling techniques, and details of operation are set forth in order to provide a more thorough understanding of the present invention. It will be appreciated, however, by one skilled in the art that the invention may be practiced without such specific details. In other instances, control structures, gate level circuits and full software instruction sequences have not been shown in detail in order not to obscure the invention. Those of ordinary skill in the art, with the included descriptions, will be able to implement appropriate functionality without undue experimentation. The invention is disclosed in the form of a microprocessor system. However, the invention may be practiced in other forms of processor such as a digital signal processor, a minicomputer, or a mainframe computer.

Figure 1:
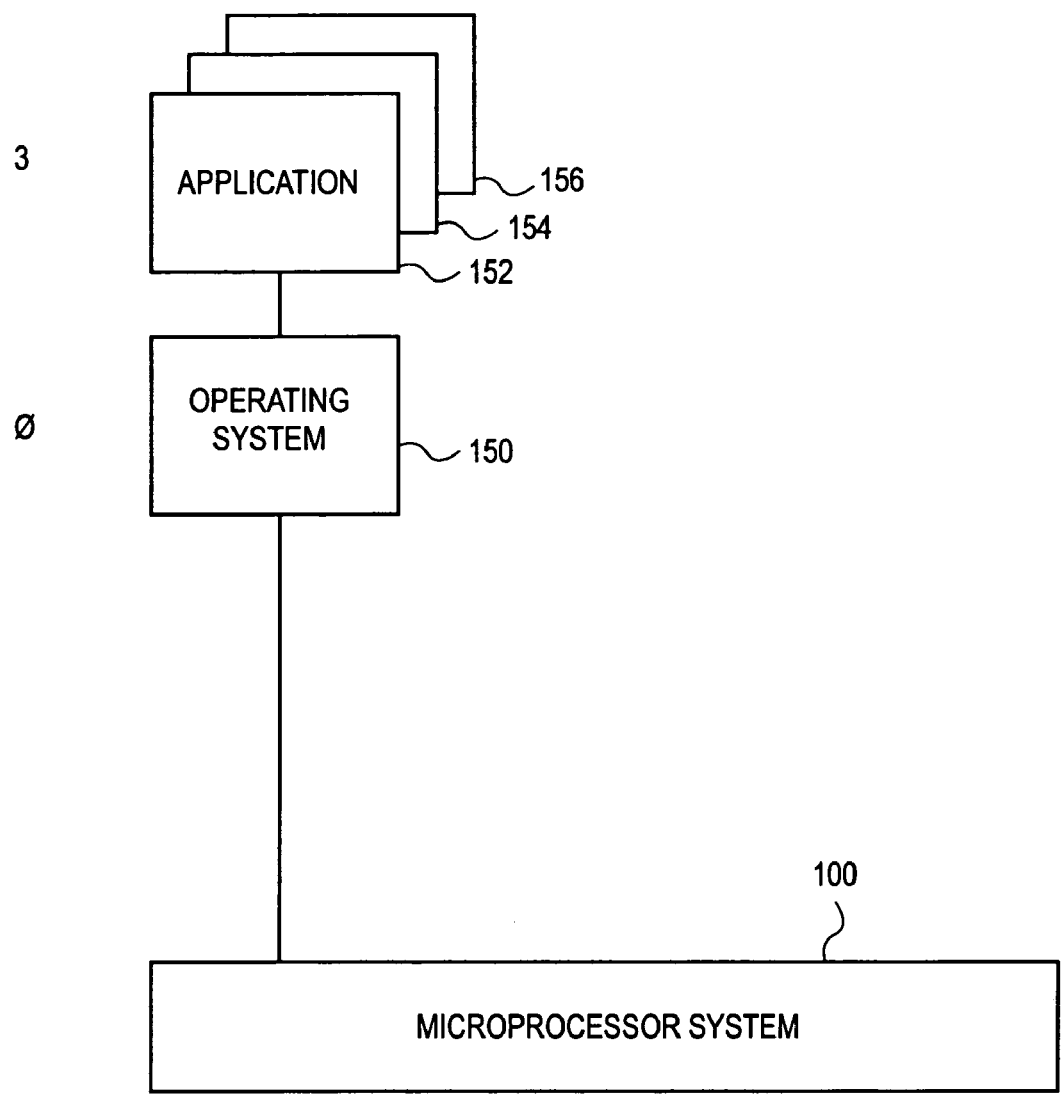
FIG. 1 is a diagram of an exemplary software environment executing in a microprocessor system.

Referring now to FIG. 1, a diagram of an exemplary software environment executing in a microprocessor system is shown. The software shown in FIG. 1 is not trusted (untrusted). When operating in a high privilege level, the size and constant updating of the operating system 150 make it very difficult to perform any trust analysis in a timely manner. Much of the operating system sits within privilege ring zero (0), the highest level of privilege. The applications 152, 154, and 156 have much reduced privilege and typically reside within privilege ring three (3). The existence of the differing privilege rings and the separation of the operating system 150 and applications 152, 154 and 156 into these differing privileged rings would appear to allow operating of the software of FIG. 1 in a trusted mode, based on making a decision to trust the facilities provided by the operating system 150. However, in practice making such a trust decision is often impractical. Factors that contribute to this problem include the size (number of lines of code) of the operating system 150, the fact that the operating system 150 may be the recipient of numerous updates (new code modules and patches) and the fact that the operating system 150 may also contain code modules such as device drivers supplied by parties other than the operating system developer. Operating system 150 may be a common one such as Microsoft® Windows®, Linux, or Solaris®, or may be any other appropriate known or otherwise available operating system. The particular types or names of applications or operating systems run or running are not critical.

Figure 2:
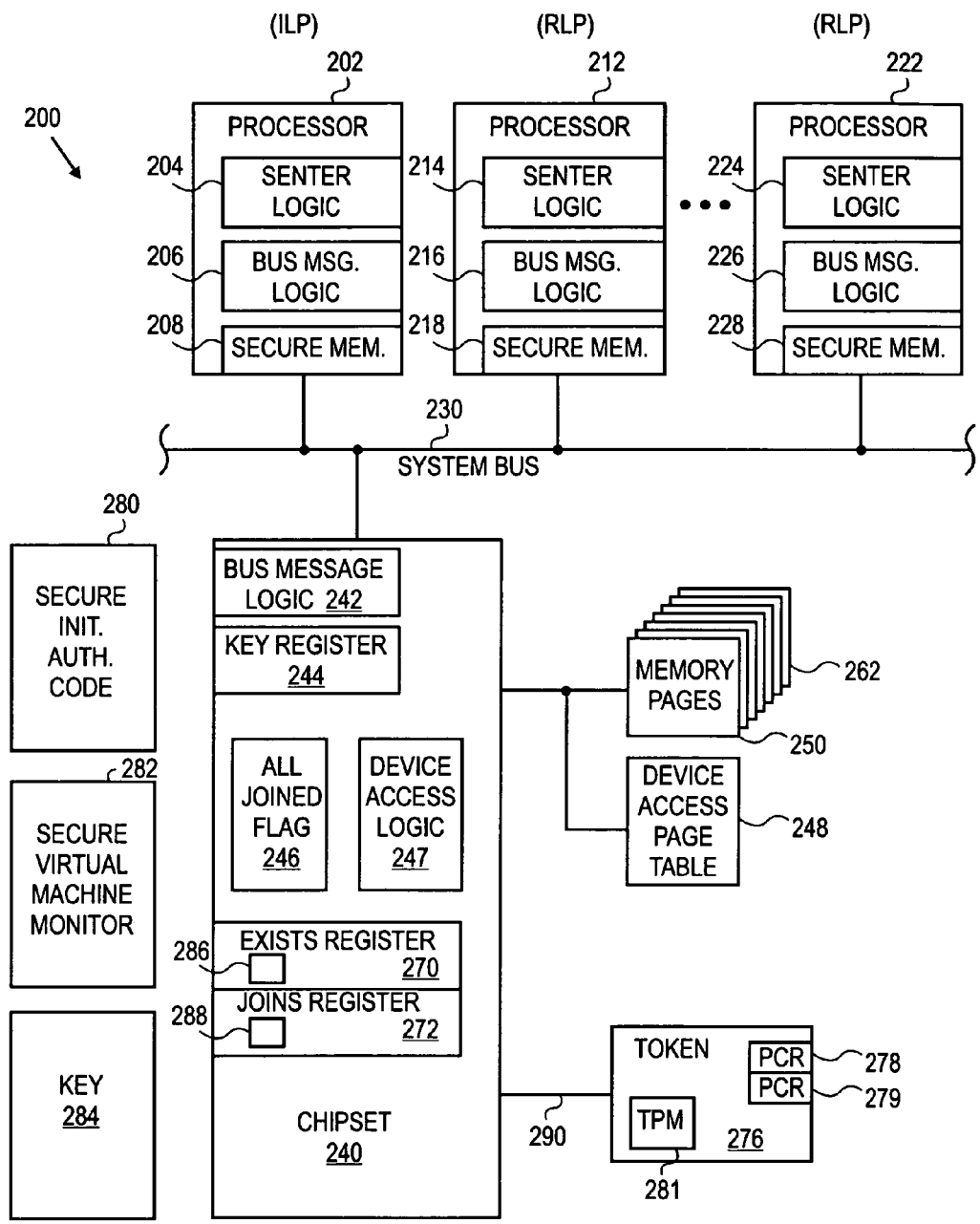
FIG. 2 is a diagram of certain exemplary trusted or secured software modules and exemplary system environment, according to one embodiment of the present invention.

Referring now to FIG. 2, a diagram of certain exemplary trusted or secured software modules and exemplary system environment 200 is shown, according to one embodiment of the present invention. In the FIG. 2 embodiment, processor 202, processor 212, processor 222, and optional other processors (not shown) are shown as separate hardware entities. In other embodiments, the number of processors may differ, as may the boundary of various components and functional units. In some embodiments the processors may be replaced by separate hardware execution threads or "logical processors" running on one or more physical processors.

Processors 202, 212, 222 may contain certain special circuits or logic elements to support secure or trusted operations. For example, processor 202 may contain secure enter (SENTER) logic 204 to support the execution of special SENTER instructions that may initiate trusted operations. Processor 202 may also contain bus message logic 206 to support special bus messages on system bus 230 in support of special SENTER operations. In alternate embodiments, memory control functions of chipset 240 may be allocated to circuits within the processors, and for multiple processors may be included on a single die. In these embodiments, special bus messages may also be sent on busses internal to the processors. The use of special bus messages may increase the security or trustability of the system for several reasons. Circuit elements such as processors 202, 212, and 222 or chipset 240 may only issue or respond to such messages if they contain the appropriate logic elements of embodiments of the present disclosure. Therefore successful exchange of the special bus messages may help ensure proper system configuration. Special bus messages may also permit activities that should normally be prohibited, such as resetting a platform configuration register 278. The ability of potentially hostile untrusted code to spy on certain bus transactions may be curtailed by allowing special bus messages to be issued only in response to special security instructions.

Additionally, processor 202 may contain secure memory 208 to support secure initialization operations. In one embodiment secure memory 208 may be an internal cache of processor 202, perhaps operating in a special mode. In alternate embodiments secure memory 208 may be special memory. Other processors such as processor 212 and processor 222 may also include SENTER logic 214, 224, bus message logic 216, 226, and secure memory 218, 228.

A "chipset" may be defined as a group of circuits and logic that support memory and input/output (I/O) operations for a connected processor or processors. Individual elements of a chipset may be grouped together on a single chip, a pair of chips, or dispersed among multiple chips, including processors. In the FIG. 2 embodiment, chipset 240 may include circuitry and logic to support memory and I/O operations to support processors 202, 212, and 222. In one embodiment, chipset 240 may interface with a number of memory pages 250 through 262 and a device-access page table 248 containing control information indicating whether non-processor devices may access the memory pages 250 through 262. Chipset 240 may include device-access logic 247 that may permit or deny direct memory access (DMA) from I/O devices to selected portions of the memory pages 250 through 262. In some embodiment the device access logic 247 may contain all relevant information required to permit or deny such accesses. In other embodiments, the device access logic 247 may access such information held in the device access page table 248. The actual number of memory pages is not important and will change depending upon system requirements. In other embodiments the memory access functions may be external to chipset 240. The functions of chipset 240 may further be allocated among one or more physical devices in alternate embodiments.

Chipset 240 may additionally include its own bus message logic 242 to support special bus messages on system bus 230 in support of special SENTER operations. Some of these special bus messages may include transferring the contents of a key register 244 to a processor 202, 212, or 222, or permitting a special ALL_JOINED flag 274 to be examined by a processor 202, 212, or 222. Additional features of the bus message logic 242 may be to register bus activity by processors in an "EXISTS" register 272 and store certain special bus message activity by processors in a "JOINS" register 272. Equality of contents of EXISTS register 272 and JOINS register 272 may be used to set the special ALL_JOINED flag 274 to indicate all processors in the system are participating in the secure enter process.

Chipset 240 may support standard I/O operations on I/O busses such as peripheral component interconnect (PCI), accelerated graphics port (AGP), universal serial bus (USB), low pin count (LPC) bus, or any other kind of I/O bus (not shown). An interface 290 may be used to connect chipset 240 with token 276, containing one or more platform configuration registers (PCR) 278, 279. In one embodiment, interface 290 may be the LPC bus (Low Pin Count (LPC) Interface Specification, Intel Corporation, rev. 1.0, 29 Dec. 1997) modified with the addition of certain security enhancements. One example of such a security enhancement would be a locality confirming message, utilizing a previously-reserved message header and address information targeting a platform configuration register (PCR) 278 within token 276. In one embodiment, token 276 may contain special security features, and in one embodiment may include the trusted platform module (TPM) 281 disclosed in the Trusted Computing Platform Alliance (TCPA) Main Specification, version 1.1a, 1 Dec. 2001, issued by the TCPA (available at the time of filing of the present application at wwwDOTtrustedpcDOTcom).

Two software components identified in system environment 200 are a Secure Virtual Machine Monitor (SVMM) 282 module and a Secure Initialization Authenticated Code (SINIT-AC) 280 module. The SVMM 282 module may be stored on a system disk or other mass storage, and moved or copied to other locations as necessary. In one embodiment, prior to beginning the secure launch process SVMM 282 may be moved or copied to one or more memory pages 250 through 262. Following the secure enter process, a virtual machine environment may be created in which the SVMM 282 may operate as the most privileged code within the system, and may be used to permit or deny direct access to certain system resources by the operating system or applications within the created virtual machines.

Some of the actions required by the secure enter process may be beyond the scope of simple hardware implementations, and may instead advantageously use a software module whose execution can be implicitly trusted. In one embodiment, these actions may be performed by Secure Initialization (SINIT) code. Three exemplary actions are identified here, but these actions should not be taken to be limiting. One action may require that various controls representing critical portions of the system configuration be tested to ensure that the configuration supports the correct instantiation of the secure environment. In one embodiment, one required test may be that the memory controller configuration provided by chipset 240 does not permit two or more different system bus addresses to touch the same location within memory pages 250 through 262. A second action may be to configure the device-access page table 248 and device-access logic 247 to protect those memory pages used by the memory-resident copy of SVMM 282 from interference by non-processor devices. A third action may be to calculate and register the SVMM 282 module's identity and transfer system control to it. Here "register" means placing a trust measurement of SVMM 282 into a register, for example into PCR 278 or into PCR 279. When this last action is taken, the trustworthiness of the SVMM 282 may be inspected by a potential system user.

The SINIT code may be produced by the manufacturer of the processors or of the chipsets. For this reason, the SINIT code may be trusted to aid in the secure launch of chipset 240. In order to distribute the SINIT code, in one embodiment a well-known cryptographic hash is made of the entire SINIT code, producing a value known as a "digest". One embodiment produces a 160-bit value for the digest. The digest may then be encrypted by a private key, held in one embodiment by the manufacturer of the processor, to form a digital signature. When the SINIT code is bundled with the corresponding digital signature, the combination may be referred to as SINIT authenticated code (SINIT-AC) 280. Copies of the SINIT-AC 280 may be later validated as discussed below.

The SINIT-AC 280 may be stored on system disk or other mass storage or in a fixed media, and moved or copied to other locations as necessary. In one embodiment, prior to beginning the secure launch process SINIT-AC 280 may be moved or copied into memory pages 250-262 to form a memory-resident copy of SINIT-AC.

Any logical processor may initiate the secure launch process, and may then be referred to as the initiating logical processor (ILP). In the present example processor 202 becomes the ILP, although any of the processors on system bus 230 could become the ILP. Neither memory-resident copy of SINIT-AC 280 nor memory-resident copy of SVMM 282 may be considered trustworthy at this time since, among other reasons, the other processors or the DMA devices may overwrite memory pages 250-262.

The ILP (processor 202) then executes a special instruction. This special instruction may be referred to as a secured enter (SENTER) instruction, and may be supported by SENTER logic 204. Execution of the SENTER instruction may cause the ILP (processor 202) to issue special bus messages on system bus 230, and then wait considerable time intervals for subsequent system actions. After execution of SENTER begins, one of these special bus messages, SENTER BUS MESSAGE, is broadcast on system bus 230. Those logical processors other than the ILP, which may be referred to as responding logical processors (RLPs), respond to the SENTER BUS MESSAGE with an internal non-maskable event. In the present example, the RLPs include processor 212 and processor 222. The RLPs must each terminate current operations, send a RLP acknowledge (ACK) special bus message on system bus 230, and then enter a wait state. It should be noted that the ILP also sends its own ACK message over system bus 230.

The chipset 240 may contain a pair of registers, "EXISTS" register 270 and "JOINS" register 272. These registers may be used to verify that the ILP and all of the RLPs are responding properly to the SENTER BUS MESSAGE. In one embodiment, chipset 240 may keep track of all operational logical processors in the system by writing a "1" into the corresponding bit of the EXISTS register 270 on any system bus transaction made by that logical processor. In this embodiment, each transaction on system bus 230 must contain an identification field containing the logical processor identifier. In one embodiment, this consists of a physical processor identifier and an indentifier for the hardware execution thread within each physical processor. For example, if a thread executing on processor 222 caused any bus transactions on system bus 230, chipset 240 would see this logical processor identifier within the transaction and write a "1" into the corresponding location 286 within EXISTS register 270. During the secure launch process, when that same thread on processor 222 sends its ACK message on system bus 230, the chipset 240 would also see this and could write a "1" into the corresponding location 288 in the JOINS register 272. (In the FIG. 2 example, each physical processor is shown with only a single thread executing for clarity. In alternate embodiments the physical processors may support multiple threads, and thereby multiple logical processors.) When the contents of the JOINS register 272 matches the contents of the EXISTS register 270, then chipset 240 can set an ALL_JOINED flag 246 indicating that all processors have properly responded to the SENTER BUS MESSAGE.

In another embodiment, EXISTS register 270 and JOINS register 272 may continue to aid security subsequent to the setting of the ALL_JOINED flag 246. During the time subsequent to the setting of the ALL_JOINED flag 246 until the end of trusted or secure operations, chipset 240 may continue to monitor and compare bus cycles against the JOINS register 272. During this period, if chipset 240 ever sees a bus transaction from a logical processor that is not currently identified in JOINS register 272, then chipset 240 may presume that this logical processor has somehow "appeared" late. This would imply that such a logical processor did not participate in the secure launch process, and therefore could represent an attacker (security threat). In such circumstances, chipset 240 may respond appropriately to keep this attacker out of the secured environment. In one embodiment, chipset 240 may force a system reset in such circumstances. In a second embodiment, similar detection of a "late" processor may be achieved by each logical processor asserting a special reserved signal on the system bus on every transaction following the assertion of the ACK bus message. In this embodiment, following the setting of the ALL_JOINED flag 246 if the chipset 240 observes a bus transaction initiated by a processor without the special signal asserted, then chipset 240 may again presume that this logical processor has somehow appeared "late", and may represent an attacker.

After issuing the SENTER BUS MESSAGE, the ILP (processor 202) polls the ALL_JOINED flag 246 to see when and if all processors have properly responded with their ACKs. If the flag 246 is never set, several implementations are possible. A watchdog timer in the ILP or chipset or elsewhere may cause a system reset. Alternatively, the system may hang requiring operator reset. In either case the assertion of a secure environment is protected (in that the secure launch process does not complete unless all processors participate), although the system may not continue to function. In normal operations, after a short time the ALL_JOINED flag 246 is set, and the ILP may be assured that all other logical processors have entered a wait state.

When the ALL_JOINED flag 246 is set, the ILP (processor 202) may move both a copy of SINIT-AC 280 and key 284 into secure memory 208 for the purpose of authenticating and subsequently executing the SINIT code included in SINIT-AC 280. In one embodiment, this secure memory 208 may be an internal cache of the ILP (processor 202), perhaps operating in a special mode. Key 284 represents the public key corresponding to the private key used to encrypt the digital signature included in the SINIT-AC 280 module, and is used to verify the digital signature and thereby authenticate the SINIT code. In one embodiment, key 284 may already be stored in the processor, perhaps as part of the SENTER logic 204. In another embodiment, key 284 may be stored in a read-only key register 244 of chipset 240, which is read by the ILP. In yet another embodiment, either the processor or the chipset's key register 244 may actually hold a cryptographic digest of key 284, where key 284 itself is included in the SINIT-AC 280 module. In this last embodiment, the ILP reads the digest from key register 244, calculates an equivalent cryptographic hash over the key 284 embedded in SINIT-AC 280, and compares the two digests to ensure the supplied key 284 is indeed trusted.

A copy of SINIT-AC and a copy of a public key may then exist within secure memory 208. The ILP may now validate the copy of SINIT-AC by decrypting the digital signature included in the copy of the SINIT-AC using the copy of a public key. This decryption produces an original copy of a cryptographic hash's digest. If a newly-calculated digest matches this original digest then the copy of SINIT-AC and its included SINIT code may be considered trustable.

The ILP may now issue another special bus message, SENTER CONTINUE MESSAGE, via system bus 230 signaling the waiting RLP's (processor 212, processor 222) and chipset 240 that secured operations are going to be initiated. The ILP may now register the unique identity of the SINIT-AC module by writing the SINIT-AC module's cryptographic digest value to a platform configuration register 272 in the security token 276, as outlined below. The ILP's execution of its SENTER instruction may now terminate by transferring execution control to the trusted copy of the SINIT code held within the ILP's secure memory 208. The trusted SINIT code may then perform its system test and configuration actions and may register the memory-resident copy of SVMM, in accordance with the definition of "register" above.

Registration of the memory-resident copy of SVMM may be performed in several manners. In one embodiment, the SENTER instruction running on the ILP writes the calculated digest of SINIT-AC into PCR 278 within the security token 276. Subsequently, the trusted SINIT code may write the calculated digest of the memory-resident SVMM to the same PCR 278 or another PCR 279 within the security token 276. If the SVMM digest is written to the same PCR 278, the security token 276 hashes the original contents (SINIT digest) with the new value (SVMM digest) and writes the result back into the PCR 278. In embodiments where the first (initializing) write to PCR 278 is limited to the SENTER instruction, the resulting digest may be used as a root of trust for the system.

Once the trusted SINIT code has completed its execution, and has registered the identity of the SVMM in a PCR, the SINIT code may transfer ILP execution control to the SVMM. In a typical embodiment, the first SVMM instructions executed by the ILP may represent a self-initialization routine for the SVMM. The ILP may in one embodiment issue individual RLP JOIN MESSAGE special bus messages to each RLP, causing each of the RLPs to join in operations under the supervision of the now-executing copy of SVMM. From this point onwards, the overall system is operating in trusted mode as outlined in the discussion of FIG. 3 below.

Figure 3:
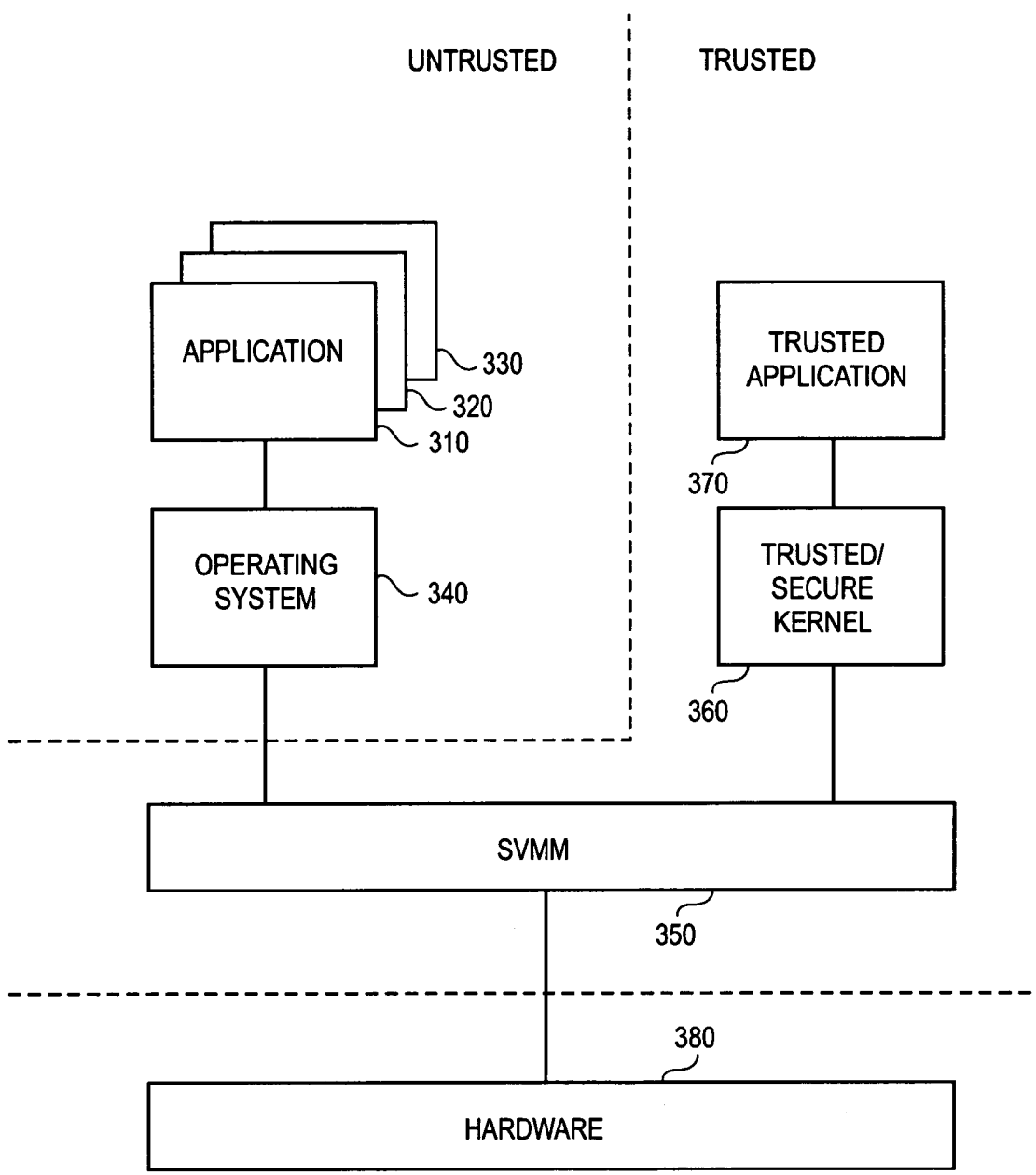
FIG. 3 is a diagram of an exemplary trusted or secured software environment, according to one embodiment of the present invention.

Referring now to FIG. 3, a diagram of an exemplary trusted or secured software environment is shown, according to one embodiment of the present invention. In the FIG. 3 embodiment, trusted and untrusted software may be loaded simultaneously and may execute simultaneously on a single computer system. A SVMM 350 selectively permits or prevents direct access to hardware resources 380 from one or more untrusted operating systems 340 and untrusted applications 310 through 330. In this context, "untrusted" does not necessarily mean that the operating system or applications are deliberately misbehaving, but that the size and variety of interacting code makes it impractical to reliably assert that the software is behaving as desired, and that there are no viruses or other foreign code interfering with its execution. In a typical embodiment, the untrusted code might consist of the normal operating system and applications found on today's personal computers.

SVMM 350 also selectively permits or prevents direct access to hardware resources 380 from one or more trusted or secure kernels 360 and one or more trusted applications 370. Such a trusted or secure kernel 360 and trusted applications 370 may be limited in size and functionality to aid in the ability to perform trust analysis upon it. The trusted application 370 may be any software code, program, routine, or set of routines which is executable in a secure environment. Thus, the trusted application 370 may be a variety of applications, or code sequences, or may be a relatively small application such as a Java applet.

Instructions or operations normally performed by operating system 340 or kernel 360 that could alter system resource protections or privileges may be trapped by SVMM 350, and selectively permitted, partially permitted, or rejected. As an example, in a typical embodiment, instructions that change the processor's page table that would normally be performed by operating system 340 or kernel 360 would instead be trapped by SVMM 350, which would ensure that the request was not attempting to change page privileges outside the domain of its virtual machine.

Figure 4A:
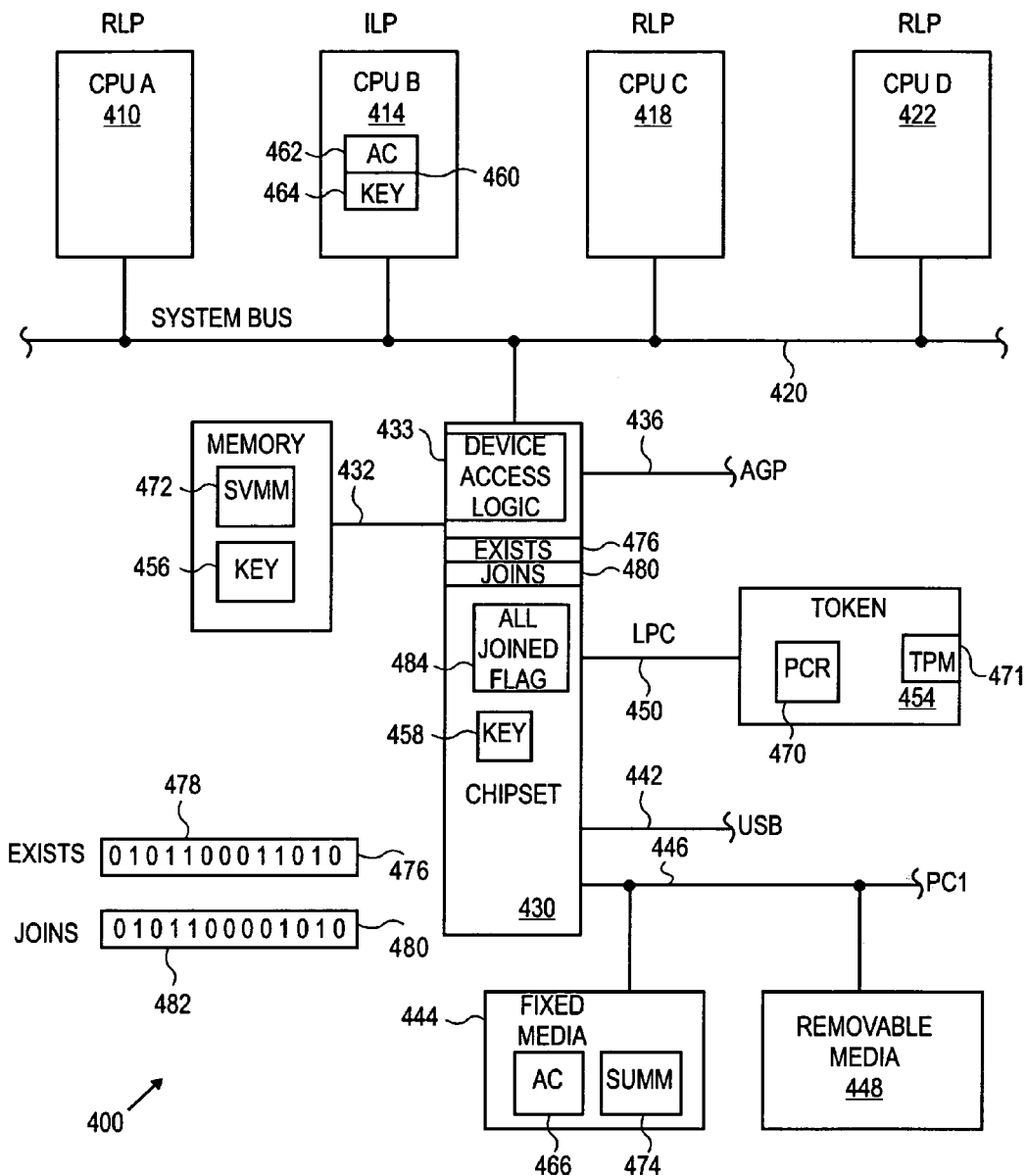
FIG. 4A is a schematic diagram of an exemplary microprocessor system adapted to support the secured software environment of FIG. 3, according to one embodiment of the present invention.

Referring now to FIG. 4A, one embodiment of a microprocessor system 400 adapted to support the secured software environment of FIG. 3 is shown. CPU A 410, CPU B 414, CPU C 418, and CPU D 422 may be configured with additional microcode or logic circuitry to support the execution of special instructions. In one embodiment, this additional microcode or logic circuitry may be the SENTER logic 204 of FIG. 2. These special instructions may support the issuance of special bus messages on system bus 420 that may enable the proper synchronization of the processors while launching the secure environment. In one embodiment, the issuance of special bus messages may be supported by circuitry such as the bus message logic 206 of FIG. 2. Similarly chipset 430 may be similar to chipset 240 and may support the above-mentioned special cycles on system bus 420. The number of physical processors may vary upon the implementation of a particular embodiment. In one embodiment, the processors may be Intel® Pentium® class microprocessors. Chipset 430 may interface with mass storage devices such as fixed media 444 or removable media 448 via PCI bus 446, or, alternately, via USB 442, an integrated controller electronics (IDE) bus (not shown), a small computer systems interconnect (SCSI) bus (not shown), or any other I/O busses. The fixed media 444 or removable media 448 may be magnetic disks, magnetic tape, magnetic diskettes, magneto-optical drives, CD-ROM, DVD-ROM, Flash memory cards, or many other forms of mass storage.

In the FIG. 4A embodiment, the four processors CPU A 410, CPU B 414, CPU C 418, and CPU D 422 are shown as four separate hardware entities. In other embodiments, the number of processors may differ. Indeed, the physically discrete processors may be replaced by separate hardware execution threads running on one or more physical processors. In the latter case these threads possess many of the attributes of additional physical processors. In order to have a generic expression to discuss using any mixture of multiple physical processors and multiple threads upon processors, the expression "logical processor" may be used to describe either a physical processor or a thread operating in one or more physical processors. Thus, one single-threaded processor may be considered a logical processor, and multi-threaded or multi-core processors may be considered multiple logical processors.

In one embodiment, chipset 430 interfaces with a modified LPC bus 450. Modified LPC bus 450 may be used to connect chipset 430 with a security token 454. Token 454 may in one embodiment include the TPM 471 envisioned by the Trusted Computing Platform Alliance (TCPA).

Figure 4B:
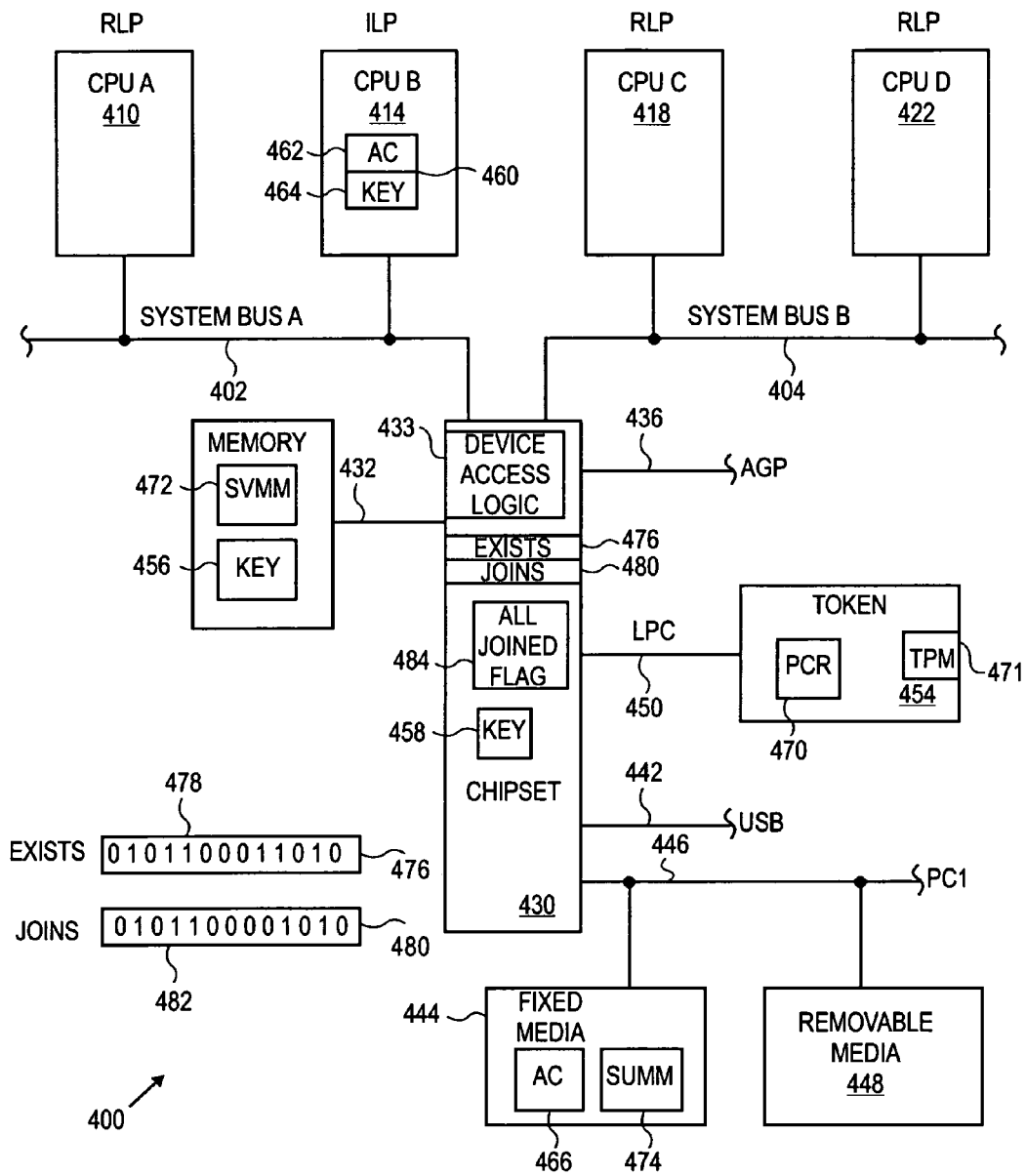
FIG. 4B is a schematic diagram of an exemplary microprocessor system adapted to support the secured software environment of FIG. 3, according to an alternate embodiment of the present invention.

Referring now to FIG. 4B, an alternate embodiment of a microprocessor system 490 adapted to support the secured software environment of FIG. 3 is shown. Differing from the FIG. 4A embodiment, CPU A 410 and CPU B 414 may be connected to chipset 428 with system bus A 402 whereas CPU C 418 and CPU D 422 may be connected to chipset 428 with system bus B 404. In other embodiments more than two system busses may be utilized. In another alternative embodiment, point-to-point busses may be used. Special instructions may support the issuance of special bus messages on system bus A 402 and system bus B 404 that may enable the proper synchronization of the processors while launching the secure environment. In one embodiment, the issuance of special bus messages may be supported by circuitry such as the bus message logic 206 of FIG. 2.

In one embodiment, chipset 428 is responsible for maintaining consistency and coherency across system bus A 402 and system bus B 404. If a bus message, standard or special, is sent across system bus A 402, chipset 428 reflects that message (when appropriate) onto system bus B 404, and vice-versa.

In an alternate embodiment, chipset 428 treats system bus A 402 and system bus B 404 as independent subsystems. Any special bus messages issued on system bus A 402 apply only to processors on that bus: similarly, special bus messages issued on system bus B 404 apply only to processors on that bus. Any protected memory that is established with respect to system bus A 402 is only accessible to processors connected to system bus A 402, and the processors on system bus B 404 may be treated as untrusted devices. To gain access to any protected memory established for CPU A 410 and CPU B 414 on system bus A 402, processors CPU C 418 and CPU D 422 on system bus B 404 must perform their own SENTER process, creating a registered environment equal to that created for the processors on system bus A 402.

Figure 5:
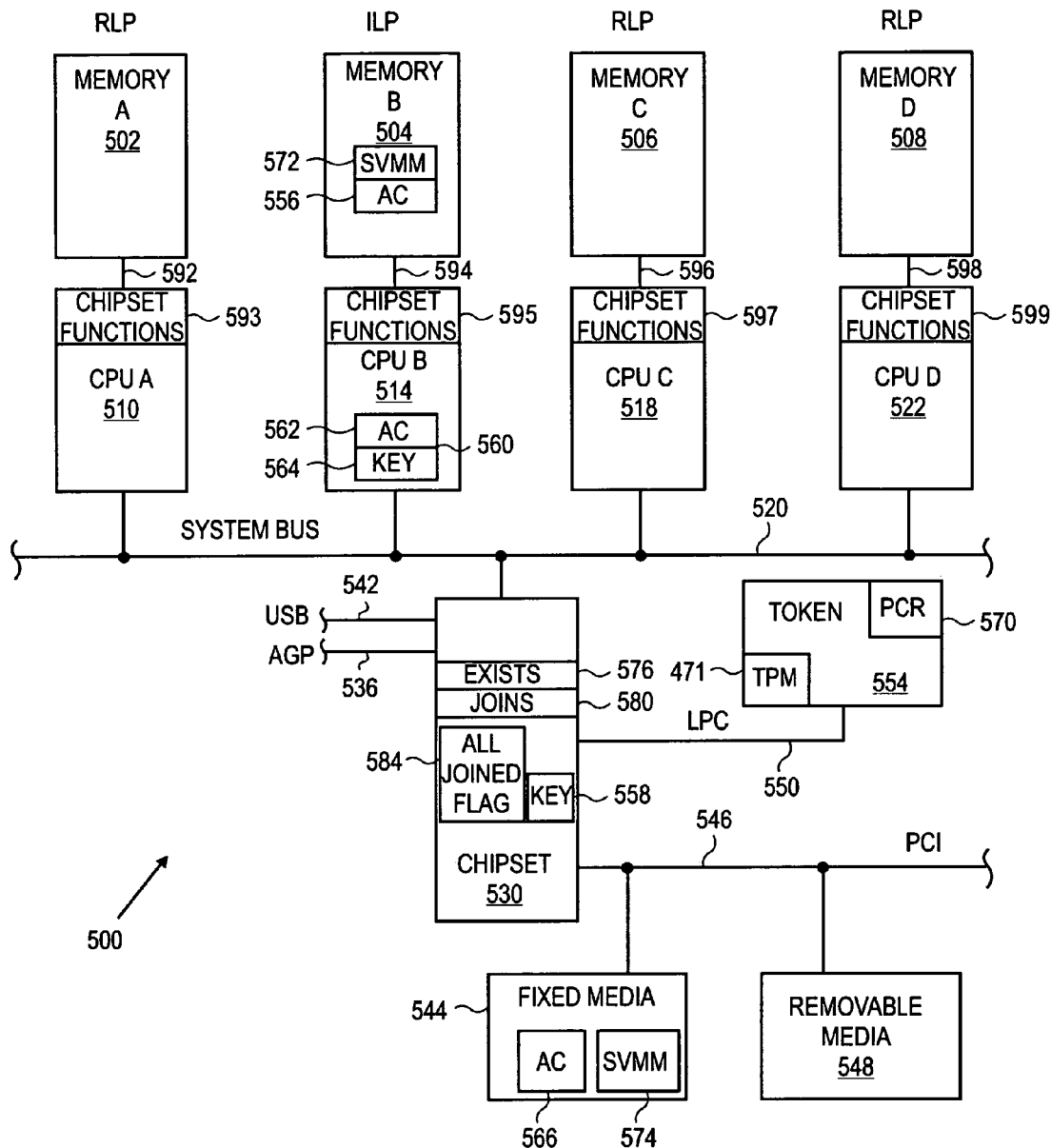
FIG. 5 is a schematic diagram of an exemplary microprocessor system adapted to support the secured software environment of FIG. 3, according to an alternate embodiment of the present invention.

Referring now to FIG. 5, a schematic diagram of an exemplary microprocessor system 500 adapted to support the secured software environment of FIG. 3 is shown, according to an alternate embodiment of the present invention. Differing from the FIG. 4A embodiment, each processor (for example, CPU A 510) may include certain chipset functions (for example, chipset functions 593) that, for example, perform memory controller functions and device access logic functions. These chipset functions thereby allow the direct connection of memory (for example, memory A 502) to the processor. Other chipset functions may remain in a separate chipset 530. Special bus messages may be issued across system bus 520.

Each processor may make indirect accesses to memory connected to other processors: however, these accesses may be considerably slower when compared to accesses to a processor's own memory. Prior to the start of the SENTER process, software may move copies of SINIT-AC 566 and SVMM 574 from fixed media 544 into local memory 504, forming copy of SINIT-AC 556 and copy of SVMM 572. In one embodiment, the memory 504 may be selected because it is directly accessed by the processor intended to be the ILP, in the FIG. 5 example this is CPU B 514. Alternatively, the SINIT-AC 566 and SVMM 574 copies may be placed in other memories attached to other (non-ILP) processors, so long as the ILP 514 has the ability to access those memories. CPU B ILP 514 begins the secure enter process by issuing the SENTER instruction, as already described in FIG. 2, and with similar consequences and bus cycles issued. Chipset 530 may utilize EXISTS register 576, JOINS register 580, and ALL_JOINED flag 584 as described above in connection with FIG. 2 to determine whether all processors have properly responded to the SENTER BUS MESSAGE and signal this information to the ILP. The ILP (CPU B 514) may again move the memory-resident copy of SINIT-AC 556 into secure memory 560, along with a copy of a public key 564. Upon verification and registration of SINIT-AC 556, ILP may then continue to verification and registration of the memory-resident copy of SVMM 572.

Figure 6:
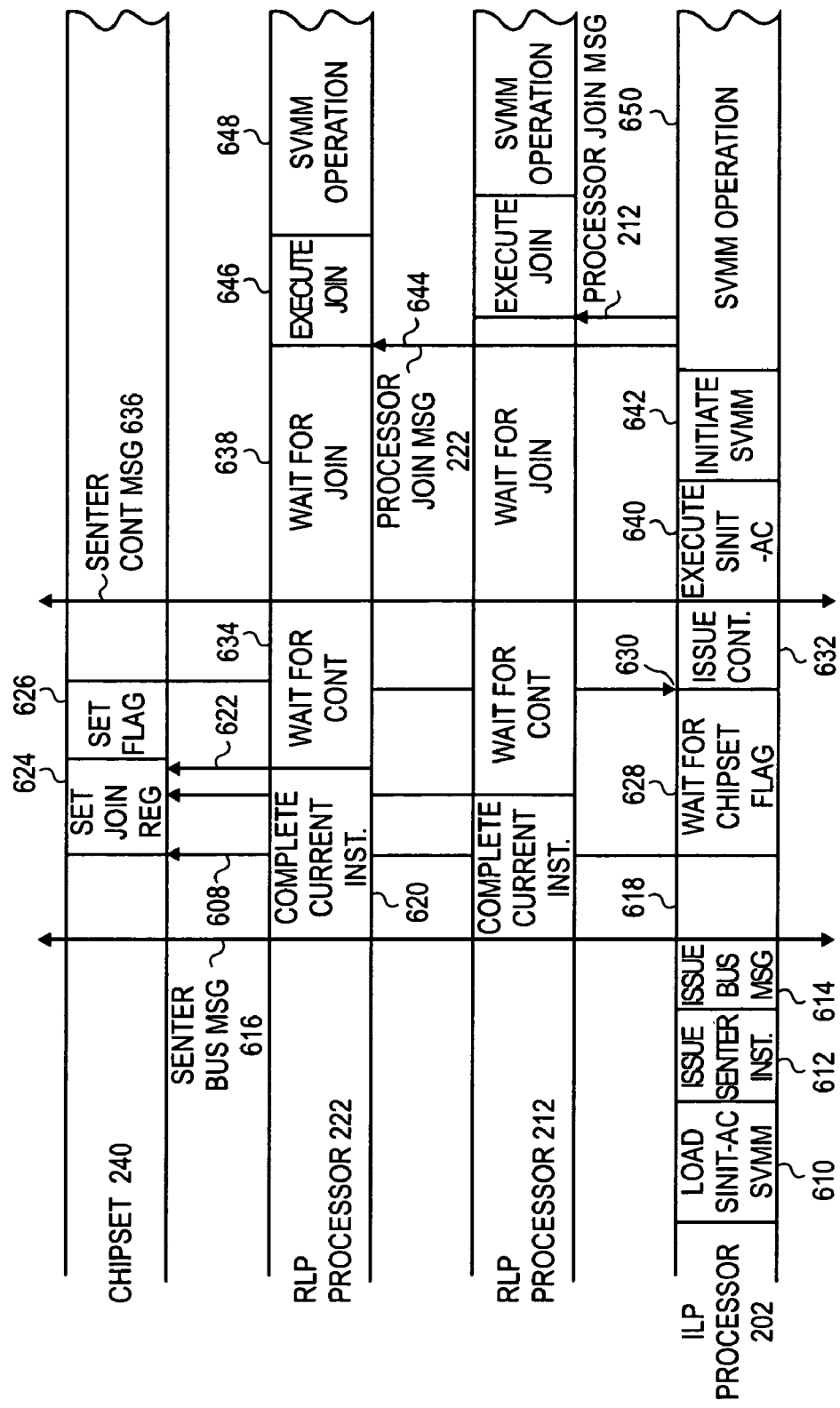
FIG. 6 is a time line drawing of the execution of software components, according to one embodiment of the present invention.

Referring now to FIG. 6, a time line drawing of various operations is shown, according to one embodiment of the present invention. The timeline of FIG. 6 shows the overall schedule of the operations discussed in connection with the exemplary system discussed in connection with FIG. 2 above. When software decides that secure or trusted operations are desired, at time 610 any software locates and makes a copy of SINIT-AC 280 and SVMM 282 available to a subsequent SENTER instruction. In this example, software loads a copy of SINIT-AC 280 and a copy of SVMM 282 into one or more memory pages 250-262. One processor, in the present example processor 202, is then selected to be the ILP, which issues the SENTER instruction at time 612. At time 614 the ILP's SENTER instruction issues the SENTER BUS MESSAGE 616. The ILP then issues its own SENTER ACK 608 at time 618 prior to entering a wait-for-chipset-flag state at time 628.

Each RLP, such as processor 222, respond to the SENTER BUS MESSAGE 616 by completing the current instruction during time 620. The RLP then issues its SENTER ACK 622 and then enters a state 634 where it waits for an SENTER CONTINUE MESSAGE.

The chipset 240 spends time 624 setting the JOINS register 272 responsive to the SENTER ACK messages observed on system bus 230. When the JOINS register 272 contents matches the EXISTS register 270 contents, chipset 240 sets the ALL_JOINED flag 246 at time 626.

During this time, the ILP may remain in a loop while polling the ALL_JOINED flag 246. When the ALL_JOINED flag 246 is set, and ILP determines that the ALL_JOINED flag 246 is set at time 630, the ILP may then issue the SENTER CONTINUE MESSAGE during time 632. When the SENTER CONTINUE MESSAGE is broadcast on system bus 230 at time 636, the RLPs may enter a wait-for-join state. For example, the RLP of processor 222 enters a wait-for-join state during time period 638.

Upon issuing the SENTER CONTINUE MESSAGE, the ILP may then (in time period 640) bring the public key of key register 244 of chipset 240 and a copy of SINIT-AC into its secure memory 208 to form a copy of the key and a copy of SINIT-AC. In another embodiment, key register 244 may contain a digest of the public key, and the actual public key may be included in, or with, the SINIT-AC. Upon authenticating the copy of SINIT-AC as described above in connection with FIG. 2, the ILP may then actually execute the copy of SINIT-AC within secure memory 208.

After the copy of SINIT-AC within secure memory 208 begins execution, it then (during time period 640) validates and registers the memory-resident copy of SVMM. After the copy of SVMM is registered in the PCR 278 of security token 276, the memory-resident copy of SVMM itself begins execution. At this time, during ongoing time period 650, SVMM operations are established in the ILP.

Among the first things that the ILP SVMM operation does is issue individual RLP JOIN MESSAGES on the system bus 230. An example is a processor 222 JOIN MESSAGE 644. This message may include a location in memory at which the RLP processor 222 may join in execution of the registered memory-resident copy of SVMM. Alternatively, the ILP SVMM operations may have registered a memory location in a predetermined location in the chipset or memory, and upon receiving the JOIN MESSAGE the RLP retrieves its starting address from this location. After receiving the processor 222 JOIN MESSAGE, and determining its starting address, during time period 646 the RLP processor 222 jumps to this location and joins execution of the registered memory-resident copy of the SVMM.

After all the RLPs have joined the registered memory-resident copy of the SVMM, secured operations are established throughout the microcomputer system 200.

Figure 7:
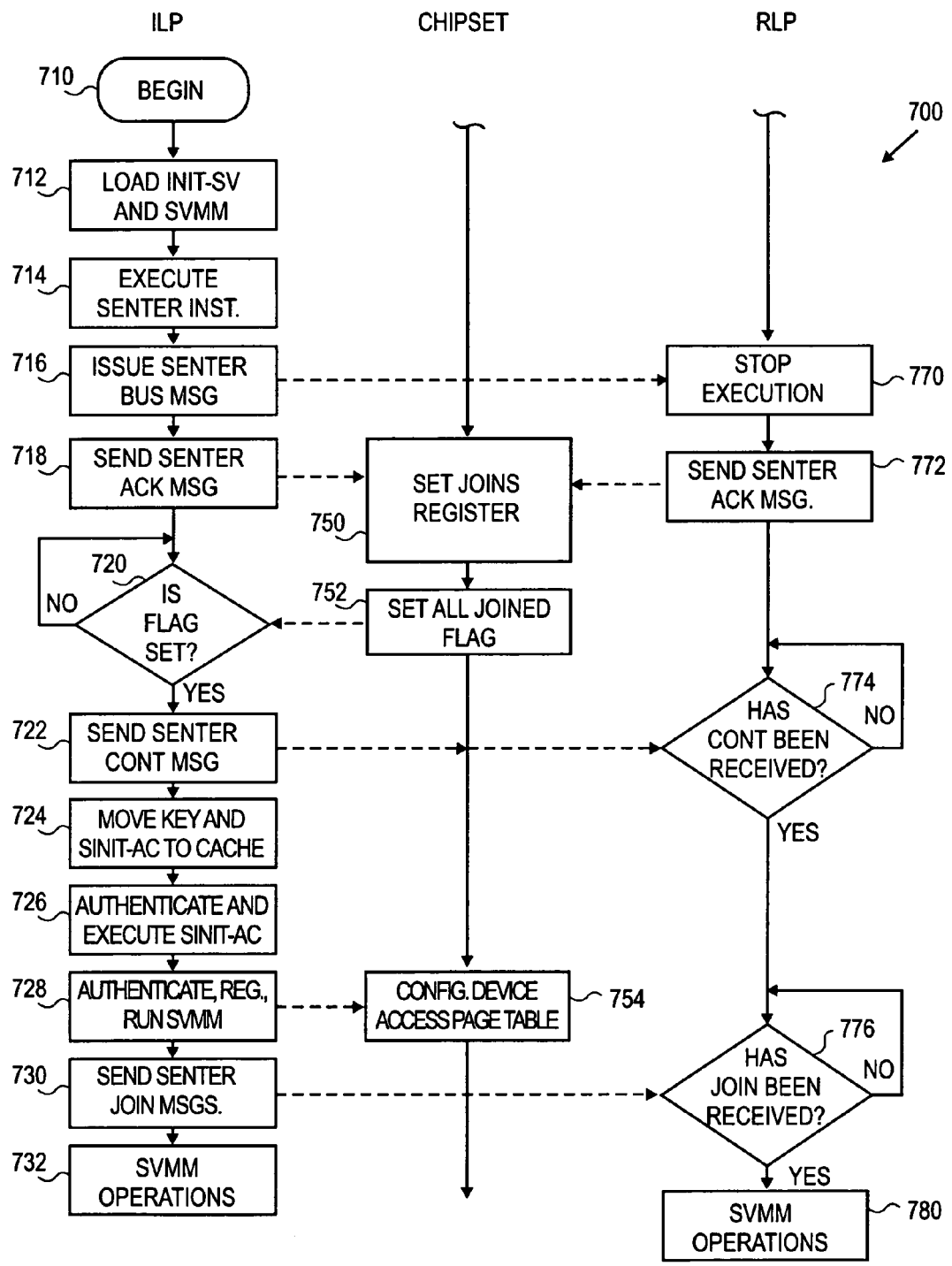
FIG. 7 is a flowchart of software and other process blocks, according to one embodiment of the present invention.

Referring now to FIG. 7, a flowchart of software and other process blocks is shown, according to one embodiment of the present invention. For the sake of clarity FIG. 7 only shows process blocks for a single representative RLP. In other embodiments there may be several responding logical processors.

The process 700 begins at block 710 when a logical processor makes a copy of the SINIT-AC and SVMM modules available for access by a subsequent SENTER instruction. In this example, in block 712 the ILP loads the SINIT-AC and SVMM code from mass storage into physical memory. In alternative embodiments, any logical processor may do so, not just the ILP. A processor becomes the ILP by executing the SENTER instruction, as identified in block 714. In block 716, the ILP SENTER instruction issues an SENTER BUS MESSAGE in block 716. The ILP then, in block 718, issues its own SENTER ACK message to the chipset. The ILP then enters a wait state, shown as decision block 720, and waits for the chipset to set its ALL_JOINED flag.

After each RLP receives the SENTER BUS MESSAGE in block 770, it halts execution with the end of the current instruction, and then in block 772 issues its own SENTER ACK. Each RLP then enters a wait state, shown as decision block 774, and waits for a SENTER CONTINUE MESSAGE to arrive from the ILP.

The chipset sets the corresponding bits in the JOINS register when SENTER ACK messages are received. When the JOINS register contents equals the EXISTS register contents, the chipset sets its ALL_JOINED flag, signaling the ILP to proceed from decision block 720.

The ILP, upon exiting decision block 720 on the YES path, then issues a SENTER CONTINUE MESSAGE in block 722. This signals each RLP to proceed from decision block 774. Each RLP then enters a second wait state, shown as decision block 776, and waits for a SENTER JOIN MESSAGE.

Meanwhile the ILP, in block 724, moves the public key of the chipset and the memory-resident copy of SINIT-AC into its own secure memory for secure execution. The ILP, in block 726, uses the key to validate the secure-memory-resident copy of SINIT-AC, and then executes it. The execution of SINIT-AC may perform tests of the system configuration and the SVMM copy, then registers the SVMM identity, and finally begins the execution of SVMM in block 728. As part of actions performed in block 728, the ILP SINIT code may configure device-access page table 248 and device-access logic 247 of memory and chipset to protect those memory pages used by the memory-resident copy of SVMM 282 from interference by non-processor devices, as shown in block 754.

After the ILP begins execution under the control of SVMM, in block 730 the ILP sends an individual SENTER JOIN MESSAGE to each RLP. After issuing the SENTER JOIN MESSAGE, the ILP then in block 732 begins SVMM operations.

The receipt of the SENTER JOIN MESSAGE causes each RLP to leave the wait state represented by decision block 776 along the YES path, and begin SVMM operations in block 780. The SENTER JOIN MESSAGE may contain the SVMM entry point the RLP branch to when joining SVMM operations. Alternatively, the ILP SVMM code may register the appropriate RLP entry point in a system location (for example, in the chipset), to be retrieved by the RLP upon receipt of the SENTER JOIN MESSAGE.

While various embodiments disclosed include two or more processors (either logical or physical processors), it should be understood that such multi-processor and/or multi-threaded systems are described in more detail to explain the added complexity associated with securing a system with multiple logical or physical processors. An embodiment also likely to be advantageous in less complex system may use only one processor. In some cases, the one physical processor may be multi-threading and therefore may include multiple logical processors (and accordingly have an ILP and an RLP as described). In other cases, however, a single-processor, single-threaded system may be used, and still utilize disclosed secure processing techniques. In such cases, there may be no RLP; however, the secure processing techniques still operate to reduce the likelihood that data can be stolen or manipulated in an unauthorized manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A processor, comprising:
   a secure memory to contain a secure initialization authenticated code; and
   secure enter logic responsive to execution of a first instruction to invoke secure operation initialization, and to detect a point in time to proceed with execution of said secure initialization authenticated code.

2. The processor of claim 1, wherein said secure memory includes first logic to load said secure initialization authenticated code.

3. The processor of claim 1, wherein said secure memory includes second logic to load keying material.

4. The processor of claim 1, wherein said secure memory includes keying material.

5. The processor of claim 1, wherein said secure enter logic to validate said secure initialization authenticated code with keying material.

6. The processor of claim 5, wherein said secure enter logic to transfer execution control to said secure initialization authenticated code when validation completes.

7. The processor of claim 5, wherein said keying material is related to a key used to encrypt a digital signature of said secure initialization authenticated code.

8. The processor of claim 5, wherein said keying material is a cryptographic digest of a key included in said secure initialization authenticated code.

9. A chipset, comprising:
   a bus messaging logic responsive to a first special bus message from a first logical processor to prepare for secure operation; and
   a key register to store keying material to be sent to said first logical processor responsive to said first special bus message.

10. The chipset of claim 9, wherein said key register to send said keying material to said first logical processor after a second logical processor sends an acknowledgment to said first special bus message.

11. The chipset of claim 10, wherein said chipset sets a flag after said bus messaging logic receives said acknowledgment.

12. The chipset of claim 9, further comprising a device access logic to lock a secure virtual machine monitor.

13. The chipset of claim 12, wherein said device access logic to receive configuration from said secure virtual machine monitor.

14. An apparatus, comprising:
   means for transmitting a special bus message;
   means for authenticating an initialization code within a first logical processor;
   means for authenticating a secure virtual machine monitor; and
   means for executing said secure virtual machine monitor in said first logical processor.

15. The apparatus of claim 14, further comprising means for transmitting an acknowledgement responsive to said first bus message.

16. The apparatus of claim 14, further comprising means for halting execution in a second logical processor and means for sending an acknowledgement.

17. The apparatus of claim 16, further comprising means for setting a flag in a chipset responsive to said acknowledgement.

18. The apparatus of claim 14, wherein said means for authenticating an initialization code includes means for moving a copy of said initialization code and a public key to a secure memory.

19. The apparatus of claim 14, wherein said means for authenticating a secure virtual machine monitor includes means for executing said initialization code.

\* \* \* \* \*